United States Patent
Plusquellic et al.

(10) Patent No.: US 9,903,808 B2
(45) Date of Patent: Feb. 27, 2018

(54) VARIABLE-FREQUENCY OPTICAL COMBS, HETERODYNE SENSOR, AND PROCESS FOR PERFORMING SPECTROSCOPY

(71) Applicant: NATIONAL INSTITUTE OF STANDARDS AND TECHNOLOGY, Gaithersburg, MD (US)

(72) Inventors: David F. Plusquellic, Boulder, CO (US); David A. Long, Bethesda, MD (US); Kevin O. Douglass, Columbia, MD (US); Joseph T. Hodges, Washington Grove, MD (US); Adam J. Fleisher, Gaithersburg, MD (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 195 days.

(21) Appl. No.: 14/590,218

(22) Filed: Jan. 6, 2015

(65) Prior Publication Data
US 2015/0159990 A1 Jun. 11, 2015

Related U.S. Application Data

(60) Provisional application No. 61/928,790, filed on Jan. 17, 2014.

(51) Int. Cl.
*G01B 9/02* (2006.01)
*G01J 3/45* (2006.01)
(Continued)

(52) U.S. Cl.
CPC ............ *G01N 21/255* (2013.01); *G01J 3/433* (2013.01); *G01J 3/453* (2013.01); *G01N 21/39* (2013.01);
(Continued)

(58) Field of Classification Search
CPC ..... G02F 2203/56; H01S 3/107; H01S 3/0057
See application file for complete search history.

(56) References Cited

U.S. PATENT DOCUMENTS 6,493,091 B2 * 12/2002 Kourogi ............ G01N 21/4795
356/489
8,724,204 B2   5/2014 Qui et al.
(Continued)

OTHER PUBLICATIONS

Zeeshan, A. et al., State-resolved THz spectroscopy and dynamics of crystalline peptide-water systems, Faraday Discussions, DOI: 10.1039/c0fd00008f (2011).
(Continued)

*Primary Examiner* — Michael A Lyons
(74) *Attorney, Agent, or Firm* — Toby D. Hain

(57) ABSTRACT

A comb source includes a continuous wave frequency source to provide a continuous wave radiation; a first modulator in optical communication with the continuous wave frequency source; a second modulator in optical communication with continuous wave frequency source; and a waveform driver in electrical communication with the first modulator and the second modulator. A process for producing an analyte spectrum includes producing a first comb from a continuous wave frequency and a first waveform; producing a reference comb and a probe comb from the first comb; subjecting a sample to the probe comb; producing a sample comb in response to subjecting the sample to the probe comb; producing a composite comb from the reference comb and the sample comb; producing a second comb from the continuous wave frequency and a second waveform; and combining the second comb and the composite comb to produce the analyte spectrum.

17 Claims, 8 Drawing Sheets

(51) Int. Cl.
  H01S 3/00    (2006.01)
  G02F 1/01    (2006.01)
  G01N 21/25   (2006.01)
  G01J 3/433   (2006.01)
  G01J 3/453   (2006.01)
  G01N 21/39   (2006.01)

(52) U.S. Cl.
  CPC .............. *G02F 1/01* (2013.01); *H01S 3/0057* (2013.01); *G01N 2021/399* (2013.01); *G02F 2203/56* (2013.01)

(56) References Cited

U.S. PATENT DOCUMENTS

| | | | |
|---|---|---|---|
| 9,046,462 B2 | 6/2015 | Pate et al. | |
| 9,115,971 B2* | 8/2015 | Kuramoto | G01B 9/02008 |
| 2012/0320448 A1* | 12/2012 | Li | G02F 1/2257 |
| | | | 359/332 |
| 2013/0025374 A1* | 1/2013 | Voskoboinik | G01D 5/35303 |
| | | | 73/655 |
| 2013/0050795 A1* | 2/2013 | Qiu | G02F 1/3536 |
| | | | 359/238 |
| 2014/0185635 A1* | 7/2014 | Cox | H01S 3/1307 |
| | | | 372/18 |
| 2014/0376077 A1* | 12/2014 | Kwon | G02F 1/365 |
| | | | 359/279 |

OTHER PUBLICATIONS

Long, D.A. et al, Multiheterodyne spectroscopy with optical frequency combs generated from a continuous-wave laser, Optics Letters vol. 39, No. 9 May 1, 2014.

Duran V. et al., Ultrafast electrooptic dual-comb interferometry, 2015.

Ferdous, F. et al., Dual-comb electric-field cross-correlation technique for optical arbitrary waveform characterization, Optics Letters, Dec. 15, 2009, 3875-3877, vol. 34, No. 24.

* cited by examiner

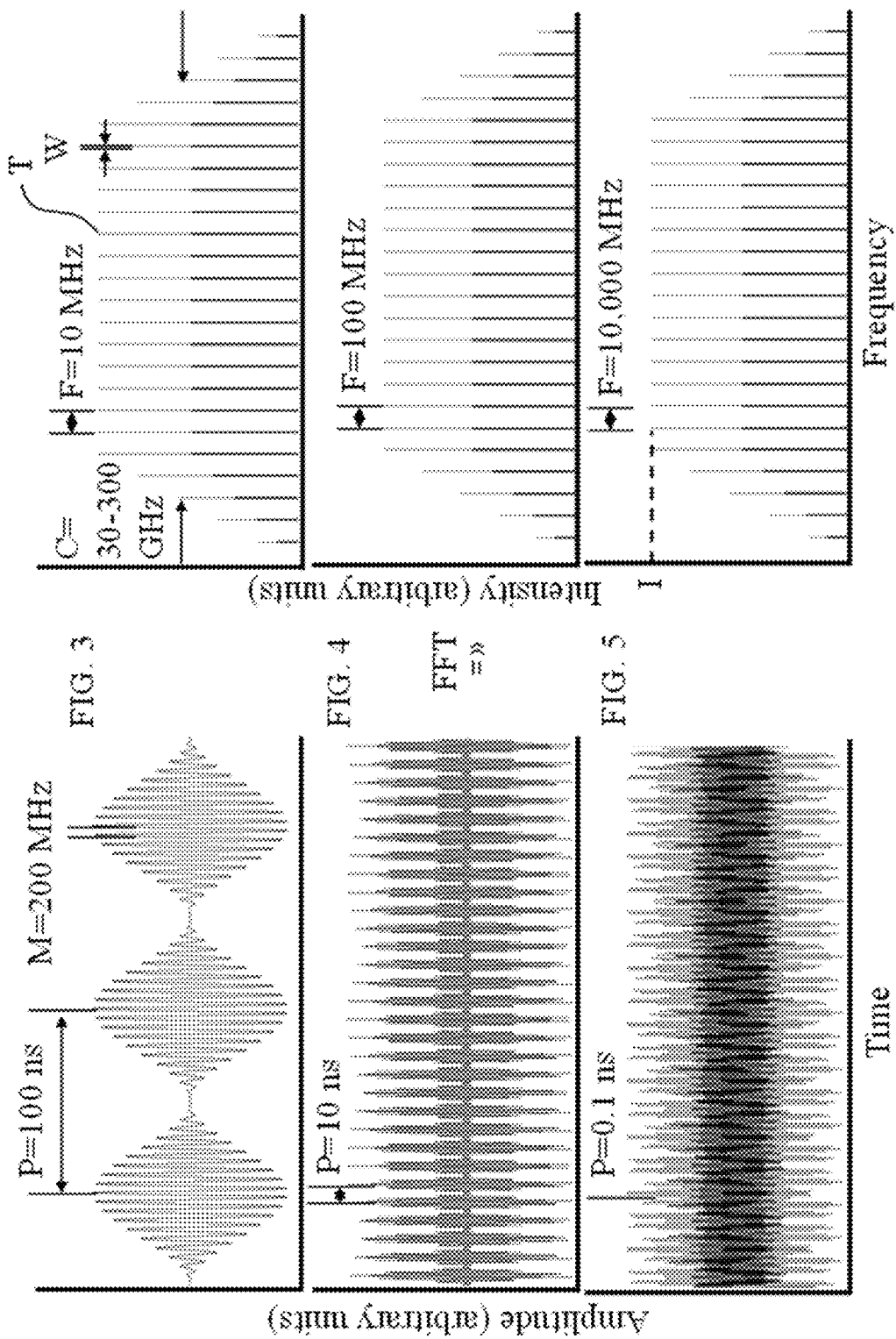

US 9,903,808 B2

VARIABLE-FREQUENCY OPTICAL COMBS, HETERODYNE SENSOR, AND PROCESS FOR PERFORMING SPECTROSCOPY

CROSS REFERENCE TO RELATED APPLICATIONS

The present application claims the benefit of U.S. Provisional Patent Application Ser. No. 61/928,790 filed Jan. 17, 2014, the disclosure of which is incorporated herein by reference in its entirety.

STATEMENT REGARDING FEDERALLY SPONSORED RESEARCH

This invention was made with United States government support from the National Institute of Standards and Technology. The government has certain rights in the invention.

BACKGROUND

Femtosecond optical frequency combs (FOFCs) generated from mode-locked pulsed lasers (MLL) offer a wide spectral bandwidth and ultra-narrow frequency component linewidths while serving as absolute frequency references when phase stabilized. However, due to the wide bandwidth of FOFCs, in some cases each frequency component has nanowatts or less of optical power that might limit ultimate sensitivity and use in spectroscopy. Furthermore, a comb spacing that is given by a repetition rate for a pulsed laser is largely fixed for a given MLL by the physical dimension of the laser cavity and physical reconstruction of the system would be required to change the comb spacing.

The art is receptive to articles and processes that provide optical frequency combs and spectroscopic applications of such combs.

BRIEF DESCRIPTION

The above and other deficiencies are overcome by, in an embodiment, a comb source comprising: a continuous wave frequency source to provide a continuous wave radiation; a first modulator in optical communication with the continuous wave frequency source to receive the continuous wave radiation; a second modulator in optical communication with continuous wave frequency source to receive the continuous wave radiation; and a waveform driver in electrical communication with the first modulator and the second modulator to provide a first waveform to the first modulator and a second waveform to the second modulator, the first waveform and the second waveform independently comprising: a variable amplitude; and a variable frequency.

Further disclosed is a heterodyne sensor comprising: the comb source; a splitter to receive the first comb and configured to split the first comb into a probe comb and a reference comb; a probe arm to receive the probe comb and comprising: a probe input configured to communicate the probe comb to a sample; and a probe output to receive a sample comb; a reference arm to receive the reference comb; a first combiner to receive the reference comb and the sample comb and configured to produce a composite comb from the reference comb and the sample comb; a local oscillator arm to receive the second comb; and a second combiner to receive the second comb from the local oscillator and the composite comb and configured to produce an analyte spectrum from the second comb and the composite comb.

Additionally disclosed is a process for producing an analyte spectrum, the process comprising: producing a first comb from a continuous wave frequency and a first waveform; producing a reference comb and a probe comb from the first comb; subjecting a sample to the probe comb; producing a sample comb in response to subjecting the sample to the probe comb; producing a composite comb from the reference comb and the sample comb; producing a second comb from the continuous wave frequency and a second waveform; and combining the second comb and the composite comb to produce the analyte spectrum.

BRIEF DESCRIPTION OF THE DRAWINGS

The following descriptions should not be considered limiting in any way. With reference to the accompanying drawings, like elements are numbered alike:

FIG. 3 shows a graph of amplitude versus time and intensity versus frequency for an embodiment of an optical frequency comb;

FIG. 4 shows a graph of amplitude versus time and intensity versus frequency for an embodiment of an optical frequency comb;

FIG. 5 shows a graph of amplitude versus time and intensity versus frequency for an embodiment of an optical frequency comb;

DETAILED DESCRIPTION

Figure 1:
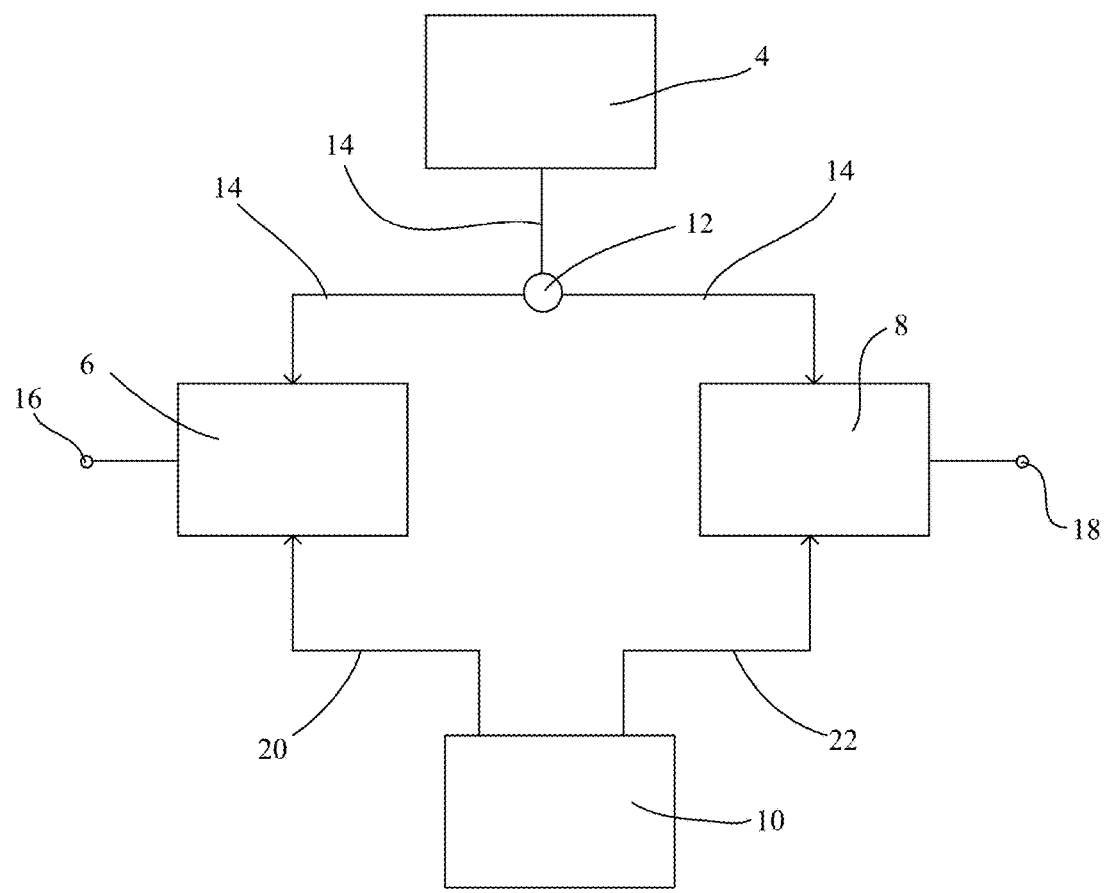
FIG. 1 shows an embodiment of a comb source.

A detailed description of one or more embodiments is presented herein by way of exemplification and not limitation.

It has been discovered that a comb source generates phase coherent optical frequency combs that include a plurality of individual frequency components (herein collectively referred to as teeth) from a continuous wave radiation source, e.g., a laser. The comb source can include a plurality of modulators (e.g., electro-optic phase modulators), a waveform driver (e.g., a single frequency microwave source or an arbitrary waveform generator), and a frequency multiplier. The optical frequency combs are generated with high fidelity from the continuous wave frequency source (e.g., a laser source) and can have a different frequency spacing among teeth in the respective combs. The combs can be subjected to high bandwidth compression and multi-heterodyne detection in a radiofrequency domain. In some embodiments, each frequency component (i.e., a tooth) is recorded and quantified to provide multiplexed spectroscopic detection of a sample, e.g., in an analyte spectrum. The arbitrary waveform generator is configured to provide a selectively tailored waveform and harmonics for production of the combs and can be used for frequency chirping.

According to an embodiment, a comb source includes a continuous wave frequency source to provide a continuous wave radiation; a first modulator in optical communication with the continuous wave frequency source to receive the continuous wave radiation; a second modulator in optical communication with the continuous wave frequency source to receive the continuous wave radiation; and a waveform driver in electrical communication with the first modulator and the second modulator to provide a first waveform to the first modulator and a second waveform to the second modulator, the first waveform and the second waveform independently include a variable amplitude; and a variable frequency or harmonic frequencies. In an embodiment, the first modulator is configured to produce a first comb in response to receipt of the first waveform and the continuous wave radiation. The second modulator is configured to produce a second comb in response to receipt of the second waveform and the continuous wave radiation. According to an embodiment, the first comb includes a plurality of first teeth. In an embodiment, the second comb includes a plurality of second teeth. In some embodiments, the first teeth are spaced apart by a first frequency spacing. In an embodiment, the second teeth are spaced apart by a second frequency spacing. The first frequency spacing and the second frequency spacing independently are selectively variable, respectively based on the first waveform and the second waveform from the waveform driver.

In an embodiment, a heterodyne sensor includes the comb source; a splitter to receive the first comb and configured to split the first comb into a probe comb and a reference comb; and a probe arm to receive the probe comb. The probe arm includes a probe input configured to communicate the probe comb to a sample and a probe output to receive a sample comb. The heterodyne sensor also includes a reference arm to receive the reference comb; a first combiner to receive the reference comb and the sample comb and configured to produce a composite comb from the reference comb and the sample comb; a local oscillator arm to receive the second comb; and a second combiner to receive the second comb from the local oscillator and the composite comb and configured to produce an analyte spectrum from the second comb and the composite comb. In an embodiment, the probe output includes a first acousto-optic modulator to receive the sample comb, and the reference arm comprises a second acousto-optic modulator to receive the reference comb. According to an embodiment, the analyte spectrum includes a plurality of heterodyned frequencies. In a particular embodiment, the plurality of heterodyned frequencies includes a radiofrequency.

In an embodiment, as shown in FIG. 1, comb source 2 includes continuous wave frequency source 4 in optical communication with first modulator 6 and second modulator 8. First modulator 6 and second modulator 8 respectively include first comb output 16 and second comb output 18.

Continuous wave frequency source 4 is configured to provide a continuous wave radiation that is communicated through optical path 14 to splitter 12. Splitter 12 splits the continuous wave radiation survey portion of the continuous wave radiation is communicated through optical path 14 to first modulator 6 and second modulator 8. Optical path 14, e.g., can be in optical medium such as a fiber optic, free space, or combination thereof. Accordingly, splitter 12 can be coupled to a fiber optic or admit the continuous wave radiation via free space propagation of the continuous wave radiation.

Waveform driver 10 is in electrical communication with first modulator 6 and second modulator 8 and is configured to produce a first waveform and the second waveform. The first waveform is communicated from waveform driver 10 to first modulator 6 through first waveform path 20. Similarly, the second waveform is communicated from waveform driver 10 to second modulator 8 through second waveform path 22. In response to receipt of the first waveform and the continuous wave radiation, first modulator 6 is configured to produce a first comb that is available for communication from first modulator 6 at first comb output 16. As used herein, "comb" refers to an optical frequency comb. In response to receipt of the second waveform of the continuous wave radiation, second modulator 8 is configured to produce a second comb that is available for communication from second modulator 8 at second comb output 18. In this manner, comb source 2 is configured to produce a plurality of combs (e.g., the first comb, second comb, and the like) from the continuous wave radiation and a plurality of waveforms (e.g., the first waveform, second waveform, and the like).

Figure 2:
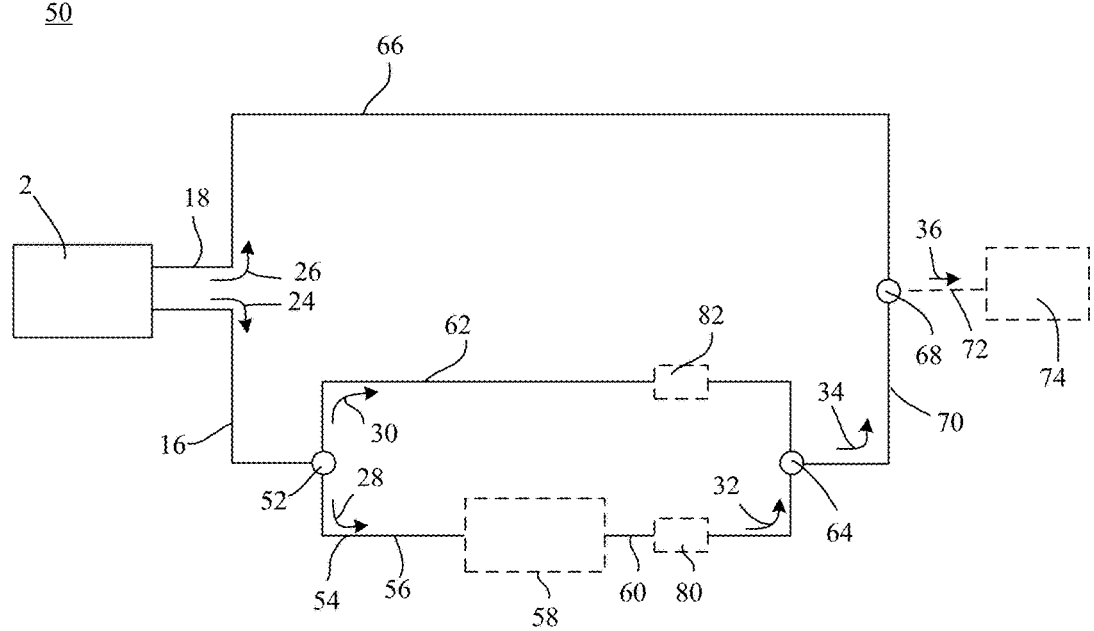
FIG. 2 shows an embodiment of a heterodyne sensor.

With reference to FIG. 2, in an embodiment, the heterodyne sensor 50 includes comb source 2 in optical communication with local oscillator arm 66 and splitter 52. Directions of propagation of optical frequency combs are shown as arrows in FIG. 2. Here, second comb 26 is communicated along second comb output 18 from comb source 2 and received by local oscillator arm 66. First comb 24 is communicated along first comb output 16 from comb source 2 and received by splitter 52. Splitter 52 is configured to optically split first comb 24 into probe comb 28 and reference comb 30. Reference arm 62 is configured to receive reference comb 30 from splitter 52 and to communicate reference comb 30 to first combiner 64.

Probe arm 54 is optically connected to splitter 52 to receive probe comb 28 and includes a probe input 56 and probe output 60. Probe arm 54 is configured to transmit probe comb 28 to probe input 56, which subjects sample 58 to probe comb 28. In response to being subjected to probe comb 28, sample 58 interacts with probe comb 28 to produce sample comb 32, e.g., through interaction of photons of probe comb 32 with sample 58. Sample comb 32 is received by probe output 60 and communicated to first combiner 64. First combiner 64 is configured to receive sample comb 32 from probe output 60 and reference comb 30 from reference arm 62. In response to receipt of sample comb 32 and reference comb 30, first combiner 64 produces composite comb 34.

In an embodiment, probe arm 54 includes first acousto-optic modulator 80 interposed between splitter 52 and first combiner 64, specifically interposed between simple 58 and first combiner 64, e.g., along probe output 60. According to an embodiment, reference arm 62 includes second acousto-optic modulator 82 interposed between splitter 52 and first combiner 64. First acousto-optic modulator 80 and second acousto-optic modulator 82 independently are configured to shift a frequency of sample comb 32 and second comb 30, respectively. It is contemplated that shifting the frequency of sample comb 32 or second comb 30 includes shifting a frequency of teeth that are included in the sample comb 32 or second comb 30.

Composite comb 34 is communicated from first combiner 64 to second combiner 68 through the sample arm 70. Second combiner 68 is configured to receive composite comb 34 and second comb 26 from local oscillator 66. In response to receipt of composite comb 34 and second comb 26, second combiner 68 produces analyte spectrum 36 that optionally can be communicated to receiver 74 through heterodyne arm 72.

First comb 24 and second comb 26 are produced by comb source 2. Here, continuous wave frequency source 4 provides the continuous wave radiation to first modulator 6 and second modulator 8. Continuous wave frequency source 4 can be a radiation source such as a laser, e.g., a solid-state laser, fiber laser, or gas laser that includes a diode laser and the like. The continuous wave radiation produced by continuous wave frequency source 4 is a continuous wave with respect to producing a plurality of first combs 24 and second combs 26 by comb source 2 without interruption of the continuous wave radiation at continuous wave frequency source 4. In an embodiment, the continuous wave radiation can be interrupted at continuous wave frequency source 4 after production of first comb 24 or second comb 26. That is, continuous wave frequency source 4 can be pulsed in a temporal domain provided continuous wave frequency source 4 emits the continuous wave radiation for a period of time great enough to produce the first plurality of teeth T1 of first comb 24 and the second plurality of teeth T2 of second comb 26.

According to an embodiment, a wavelength of the continuous wave radiation is effective to produce first comb 24 and second comb 26. In an embodiment, the wavelength of the continuous wave radiation can be from 300 nanometers (nm) to 100000 nm, specifically 700 nm to 3000 nm. A power of the continuous wave radiation is effective to produce first comb 24 and second comb 26. In a particular embodiment, the power of the continuous wave radiation is less than a damage threshold of optical elements (e.g., fiber optic lines, mirrors, lenses, and the like) in comb source 2 or heterodyne sensor 50. The art of the continuous wave radiation can be from 500 microwatts (µW) to 100 W. It should be appreciated that the power of the continuous wave radiation can be selected to produce a certain pulse peak power among first teeth T1 in first comb 24 or second teeth T2 in second comb 26.

Propagation or communication of the continuous wave radiation, first comb 24, second comb 26, probe comb 28, reference comb 30, a sample comb 32, composite comb 34, or analyte spectrum 36 occurs in free space, an optically conductive medium effective to communicate electromagnetic radiation included in the continuous wave radiation and combs (24, 26, 28, 30, 32, 36, and the like), or combination of free space and the optically conductive medium. That is optical path 14, splitter 52, reference arm 62, probe arm 54, local oscillator arm 66, sample arm 70, and heterodyne arm 72 independently include free space, optically conductive media, or combination thereof. The optically conductive medium can include optical elements such as fiber optic cable, lenses, mirrors, beam splitters, optical filters, and the like.

Waveform driver 10 provides the first waveform to first modulator 6 and the second waveform to the second modulator 8. Accordingly, waveform driver 10 produces a waveform that includes a plurality of voltage pulses in the temporal domain. In an embodiment, a frequency of the voltage pulses is effective selected to drive first modulator 6 and second modulator 8 respectively to produce first comb 24 and second comb 26. The frequency of the voltage pulses can be from a radiofrequency to a terahertz frequency. In a particular embodiment, the frequency the voltage pulses is a microwave frequency. An exemplary frequency of the voltage pulses is from 1 kilohertz (kHz) to 50 (GHz). According to an embodiment, the frequency of the voltage pulses is constant. In a particular embodiment, waveform driver 10 produces voltage pulses that include a variable amplitude, variable frequency, or combination thereof. A peak-to-peak voltage amplitude of the voltage pulses can be from a minimum voltage to drive first modulator 6 or second modulator 8 to slightly below a voltage damage threshold of first modulator 6 or second modulator 8. In a particular embodiment, the peak-to-peak voltage amplitude of voltage pulses can be from 50 µV to 150 V, specifically 10 millivolts (mV) to a TTL logic level (e.g., 3.2 V). Accordingly, first waveform 24 and second waveform 26 have a selectively variable amplitude, selectively variable frequency, or combination thereof. In some embodiments, waveform driver 10 is a frequency synthesizer such as a microwave synthesizer. In a certain embodiment, waveform driver 10 is an arbitrary waveform generator.

According to an embodiment where waveform driver 10 is the arbitrary waveform generator, the first waveform and the second waveform respectively are arbitrary waveforms having a selective amplitude and a selected frequency or harmonic frequencies that may be changed by waveform driver 10. Waveform driver 10 can include independent output channels to output the first waveform independent from the second waveform with respect to a parameter such as relative timing of the voltage pulses in the first waveform and the second waveform. The relative timing of which can be selected as an input to waveform driver 10. Moreover, waveform driver 10 in certain embodiments can be programmed to produce a desired first waveform or second waveform. Programming waveform driver 10 can include using a genetic algorithm to produce a selected amplitude or selective frequency or harmonic frequencies to be produced by waveform driver 10.

First modulator 24 and second modulator 26 respectively receive the continuous wave radiation from continuous wave frequency source 4 to respectively produce first comb 24 and second 26. First modulator 24 second modulator 26 also respectively receive the first waveform and second waveform from waveform driver 10. The first waveform and second waveform respectively control first modulator 24 and second modulator 26 to selectively modulate the input continuous wave radiation to produce modulated radiation output, specifically first comb 24 and second comb 26. Exemplary modulators for first modulator 24 and second modulator 26 independently are an electro-optic modulator such as a phase modulator, Pockels cell, Mach-Zehnder modulator (including a dual drive Mach-Zehnder modulator), or a combination thereof.

In an embodiment, first comb 24 includes the plurality of first teeth T2, and second comb 26 includes the plurality of second teeth T2. With reference to FIG. 3, showing a graph of intensity versus frequency for a comb (e.g., first comb 24 or second comb 26), teeth T (e.g., first teeth T1 or second teeth T2) have an amplitude of intensity I and are spaced apart by a frequency spacing F (e.g., first frequency spacing F1 or second frequency spacing F2). In second comb 26, the second teeth are spaced apart by the second frequency spacing F2. According to an embodiment, first frequency spacing F1 and second frequency spacing F2 independently are selectively variable, respectively, based on a frequency of voltage pulses in the first waveform and the second waveform from waveform driver 10. In some embodiments, first frequency spacing F1 is different than second frequency spacing F2. According to an embodiment, first frequency spacing F1 and second frequency spacing F2 are independently selectively tunable from 1 kHz to 50 GHz. Such selective tunability of first frequency spacing F1 and second frequency spacing F2 is determined by the frequency of the pulses in the first waveform and the second waveform provided by waveform driver 10.

In a specific embodiment, first modulator 6 and second modulator 8 are dual drive Mach-Zehnder modulators as described in Long et al., "Multiheterodyne Spectroscopy with Optical Frequency Combs Generated from a Continuous-wave Laser," Optics Letters 39, 2688 (2014), the disclosure of which is incorporated by reference herein in its entirety. In this manner, first comb 24 and second comb 26 independently are a power-leveled optical frequency comb.

An exemplary first comb is shown in FIG. 3, wherein the first comb has a maximum intensity I of first teeth T1 that have first frequency spacing F1, and individual teeth have pulse width W1 (e.g., at full width at half maximum (FWHM) of individual tooth). Since the maximum intensities I of all first teeth T are substantially uniform, first comb 24 is power-leveled. Here, first frequency spacing F1 is 10 MHz produced by providing the first waveform having a amplitude modulated period of 100 nanoseconds (nsec) and waveform frequency M of 200 MHz to first modulator 6 such that the continuous wave from the continuous wave frequency source was amplitude modulated at 10 MHz to produce first teeth T1. Furthermore, each first teeth T1 are replicated at each EOM sideband frequency with spacing M of 200 MHz (not shown, See FIG. 15). FIGS. 4 and 5 respectively show graphs of intensity versus frequency for first combs 24 having first frequency spacing F1 of 100 MHz and 10 GHz, determined by the first waveforms having a amplitude modulated period of 10 ns (FIG. 4) or 0.1 ns (FIG. 5), respectively. First frequency spacing F1 also may be determined by waveform frequencies M determined from unmodulated waveforms (i.e., no amplitude modulation). Furthermore, amplitude modulation also may be done using an additional modulator in series with EOM. Second comb 26 has properties similar to first comb 24 in an embodiment. In some embodiments, first frequency spacing F1 of first comb 24 is different than second frequency spacing F2 of second comb 26. In some embodiments, first frequency spacing F1 of first comb 24 and second frequency spacing F2 of second comb 26 are generated by amplitude modulated and unmodulated waveforms, respectively.

First teeth T1 and second teeth T2 independently include pulse period P and pulse shape or waveform frequency M (see FIG. 3). Pulse period and shape or waveform frequency can be selected with respect to an absorption linewidth of sample 58, frequency spacing F, optical power of first teeth 24 or second teeth 26, bandwidth C of first comb 24 or second comb 26, and the like. In an embodiment, waveform frequency is greater than 100 MHz, specifically from 10 MHz to 20 GHz, and more specifically from 200 MHz to 18 GHz. In an embodiment, pulse period is greater than 0.1 nanoseconds (nsec), specifically from 0.1 nsec to 1000 nsec, and more specifically from 10 nsec to 100 nsec. A maximum intensity (e.g., fluence and the like) or optical power in the teeth can be selected based on an absorption cross-section of sample 58, frequency spacing F, bandwidth of first comb 24 or second comb 26, characteristics of first modulator 6 or second modulator 8 (e.g., frequency response), damage threshold of optical or electro-optical components, and the like. The power of power leveled first teeth T1 or second teeth T2 can be from 100 fW to 100 W, specifically from 10 μW to 10 mW, and more specifically from 10 μW to 100 μW.

In an embodiment, second comb 26 is communicated to local oscillator arm 66 of heterodyne sensor 50, and first comb 24 is communicated to splitter 52, which splits first comb 16 into reference comb 30 communicated to reference arm 62 and probe comb 28 communicated to probe arm 54. Sample 58 is subjected to probe comb 28 to produce sample comb 32, which is received by probe output 60. According to an embodiment, first acousto-optic modulator 80 is interposed between sample 58 and first combiner 64 to receive sample comb 32 and to shift a frequency of the plurality of teeth in sample comb 32. Here, each tooth in sample comb 32 is shifted by a same amount in a frequency domain such that first frequency spacing among the plurality of first teeth is maintained.

In some embodiments, probe comb 28 and sample comb 32 differ because probe comb 28 interacts with sample 58 such that sample 58 absorbs and phase shifts some of the power from a tooth of probe comb 28. In a certain embodiment, probe comb 28 and sample comb 32 differ because sample comb 32 is communicated through first acousto-optic modulator 84 being received by first combiner 64 such that the plurality of teeth in sample comb 32 occur at a different frequency with respect to the plurality of teeth in probe comb 28.

According to an embodiment, reference arm 62 includes second acousto-optic modulator 82 that is configured to receive reference comb 30 and to shift a frequency of the plurality of teeth in reference comb 30. It is contemplated that first acousto-optic modulator 80 and second acousto-optic modulator 82 shift the frequencies of the plurality of teeth in sample comb 32 and reference comb 30 by a same amount. The shift in frequency of the reference comb 30 (by second acousto-optic modulator 82) and sample comb 32 (by first acousto-optic modulator 80) can be from 10 (Hertz) Hz to 1 GHz, specifically from 1 MHz to 700 MHz, more specifically 20 MHz to 250 MHz, and further specifically a radiofrequency. In an embodiment, the shift in frequency is 20 MHz to 250 MHz to provide analyte spectrum 36 (after composite comb 34 is combined with second comb 26) that includes a plurality of teeth in a radiofrequency range.

After being subjected to first acousto-optic modulator 80 and second acousto-optic modulator 82, sample comb 32 and reference comb 30 are combined by first combiner 64 to produce composite comb 34, which is combined with second comb 26 by second combiner 68 to produce analyte spectrum 36. Analyte spectrum 36 is detected by receiver 74. Exemplary receivers include a photodiode, photomultiplier, frequency analyzer, and the like. In an embodiment, receiver 74 is a photodiode that receives composite comb 34 and second comb 26 from second combiner 68 and is in electrical communication with a frequency analyzer, which is optionally connected to a microprocessor, memory storage medium, computer, analog-to-digital converter, and the like to process or store data from receiver 74.

Sample 58 produces sample comb 32 in response to being subjected to probe comb 28. In an embodiment, sample 58 is supported on platform and probe comb 28 is provided to sample 58 via probe input 56 and sample comb 32 is communicated from sample 58 to probe output 60. Exemplary samples include a solid, liquid, gas, or combination thereof that interact with probe comb 28 to produce sample comb 32. In a certain embodiment, sample 58 is disposed in a sample container. The sample container includes an entry port that is configured to receive probe comb 28 and is selected to transmit probe comb 28 to sample 58 without substantially modifying a phase or amplitude of probe comb 28. An exit port is provided in the sample container to communicate sample comb 32 to probe output 60 without substantially modifying a phase or amplitude of sample comb 32. The sample container can be, e.g., a gas cell, vacuum chamber, flow cell, optical cavity, multi-pass cell, open to atmosphere, spectrometer, and the like. Further, the sample container can be a closed container to fully enclose sample 58 disposed therein. In some embodiments, the sample container is an open container such that sample 58 can be exposed to the environment external to the sample container or transmitted through the atmosphere for remote sensing.

According to an embodiment, a process for producing analyte spectrum 36 includes producing first comb 24 from the continuous wave frequency and the first waveform, producing reference comb 30 and probe comb 28 from first comb 24; subjecting sample of 58 to probe comb 28; producing sample comb 32 in response to subjecting the sample to probe comb 28; producing composite comb 34 from reference comb 30 and sample comb 32; producing second comb 26 from the continuous wave frequency and the second waveform; and combining second comb 26 (from local oscillator arm 66) and composite comb 34 to produce analyte spectrum 36. Here, reference comb 30 and sample comb 32 each include plurality of first teeth T1 that are spaced apart by first frequency spacing F1. Second comb 26 includes the plurality of second teeth T2 that are spaced apart by second frequency spacing F2, and first frequency spacing F1 is different than second frequency spacing F2. The process also includes changing a frequency spacing of the plurality of first teeth T1 prior to combining second comb 26 and composite comb 34. Combining second comb 26 and composite comb 34 includes heterodyning the plurality of first teeth T1 with the plurality of second teeth T2 such that analyte spectrum 36 includes a plurality of teeth that have a frequency that is a radiofrequency.

In an embodiment, multiheterodyne spectroscopy is performed by producing first comb 24 and second comb 26 from the continuous wave frequency source (e.g., a diode laser). First comb 24 and second comb 26 have different comb spacings, i.e., first frequency spacing F1 is different than second frequency spacing F2. Probe comb 28 produced from the first comb 24 probes sample 58 (e.g., a gas sample disposed in the sample container), and second comb 26 is a local oscillator (LO) in local oscillator arm 66. The two optical frequency combs (OFCs, first comb 24 and second comb 26) are combined on a photodiode for bandwidth compression and detection in a radio frequency (RF) domain. Each optical frequency component (i.e., tooth) of composite comb 34 includes a unique RF beat frequency with the LO (second comb 26) in the heterodyne signal of analyte spectrum 36. Accordingly, the entire OFC of analyte spectrum 36 is simultaneously received or recorded by receiver 74, e.g., a spectrum analyzer. It should be appreciated that heterodyne sensor 50 does not include mechanical motion of its elements (unlike Fourier-transform spectroscopy, which uses a moving mirror). Moreover, the heterodyne sensor 50 provides for high speed measurements of analyte spectrum 36.

In an embodiment, first comb 24 and second comb 26 are generated using dual-drive Mach-Zehnder modulators (MZM) as first modulator 6 and second modulator 8. To produce dual drive control waveforms to first modulator 6, the first waveform from waveform driver 10 is split into two waveforms where one of the two waveforms is attenuated in amplitude before the two waveforms are provided to first modulator 6. Similarly, to produce dual drive control waveforms to second modulator 8, the second waveform from waveform driver 10 is split into two waveforms where one of the two waveforms is attenuated in amplitude before the two waveforms are provided to second modulator 8. In this manner, first modulator 6 and second modulator 8 respectively power level the resultant first comb 24 and second comb 26 by attenuation of an input drive from an input waveform (i.e., the first waveform or the second waveform) used to control the MZMs (i.e., first modulator 6 and second modulator 8). Control of a phase condition of output first comb 24 and second comb 26 is accomplished by providing an external DC bias to first modulator 6 and second modulator 8. Thereafter, first comb 24 is split by splitter 52 into probe comb 28 and reference comb 30. Probe comb 28 is used to probe sample 58 that produces sample comb 32.

Figure 6:
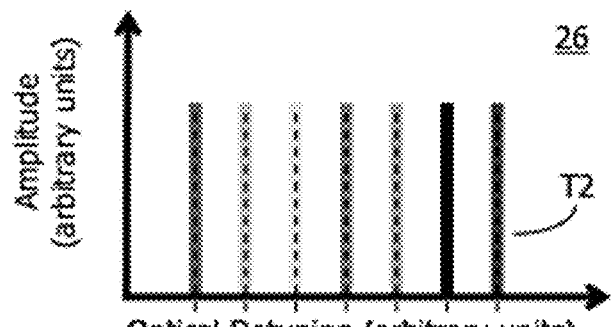
FIG. 6 shows a graph of amplitude versus optical detuning for an embodiment of a local oscillator comb.

FIG. 6 shows a graph of amplitude versus optical detuning for an exemplary sample comb 30 from local oscillator arm 66 and that has second teeth T2 separated by second frequency spacing F2. Here, a frequency ($f_{n,LO}$) for second teeth T2 of second comb 26 is given by equation 1 as follows:

$$f_{n,LO} = n \times f_{mod} + f_0 \qquad (1),$$

wherein n is an integer (−n, ..., −2, −1, 0, 1, 2, ..., n); $f_{mod}$ is the frequency of the second waveform provided to second modulator 8; and $f_0$ is an optical carrier frequency (i.e., a frequency of a continuous wave frequency source 4).

Figure 7:
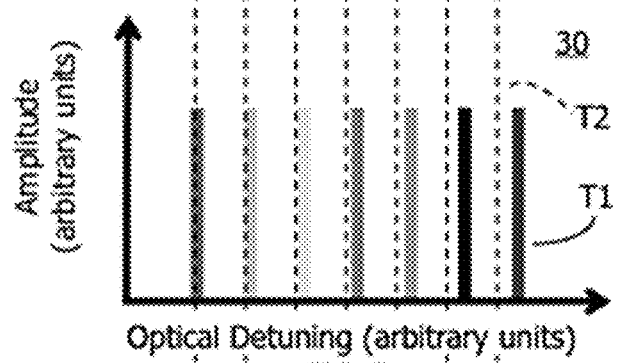
FIG. 7 shows a graph of amplitude versus optical detuning for an embodiment of a second comb communicated through a reference arm.

FIG. 7 shows a graph of amplitude versus optical detuning for an exemplary reference comb 30 that has first teeth T1 separated by first frequency spacing F1. Here, a frequency ($f_{n,Ref}$) for first teeth T1 of reference comb 30 is given by equation 2 as follows:

$$f_{nRef} = n \times (f_{mod} + \delta f_{mod}) + f_0 + f_{AOM,82} \qquad (2),$$

wherein n, $f_{mod}$, and $f_0$ are recited for second comb 26 in FIG. 6; $\delta f_{mod}$ is a frequency difference between reference comb 30 and second comb 26 carried by local oscillator arm 66; and $f_{AOM,82}$ is the frequency of acousto-optic modulator 82. For comparison with second comb 26 from local oscillator arm 66, frequency positions of the plurality of second teeth T2 in second comb 26 are shown as dashed lines in FIG. 7.

Figure 8:
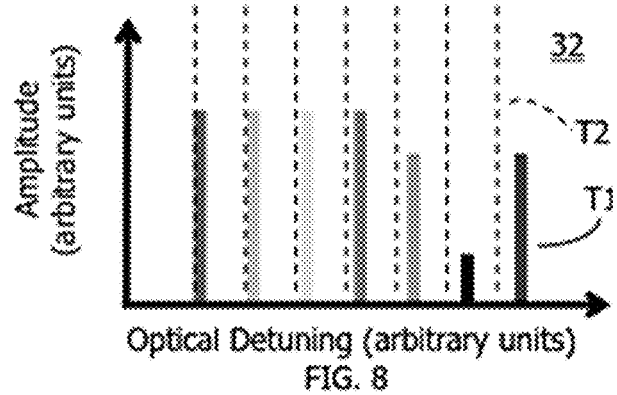
FIG. 8 shows a graph of amplitude versus optical detuning for an embodiment of the second comb (referred with regard to FIG. 7) communicated through a probe arm and analyte, resulting in a sample comb.

FIG. 8 shows a graph of amplitude versus optical detuning for an exemplary sample comb 32 that has first teeth T1 separated by first frequency spacing F1. Here, a frequency ($f_{n,sample}$) for first teeth T1 of sample comb 32 is given by equation 3 as follows:

$$f_{n,sample} = n \times (f_{mod} + \delta f_{mod}) + f_0 + f_{AOM,80} \qquad (3),$$

wherein n, $f_{mod}$, $\delta f_{mod}$, and $f_0$ are for second comb 26 and reference comb 30 in FIGS. 6 and 7, and $f_{AOM,80}$ is the frequency of acousto-optic modulator 80. It should be appreciated that sample comb 32 is produced from interaction of probe comb 28 with sample 58 to and subsequent shifting of the frequency of the output from sample 58 by first acousto-optic modulator 80. For comparison with second comb 26 from local oscillator arm 66, frequency positions of the plurality of second teeth T2 in second comb 26 are shown as dashed lines in FIG. 8

Figure 9:
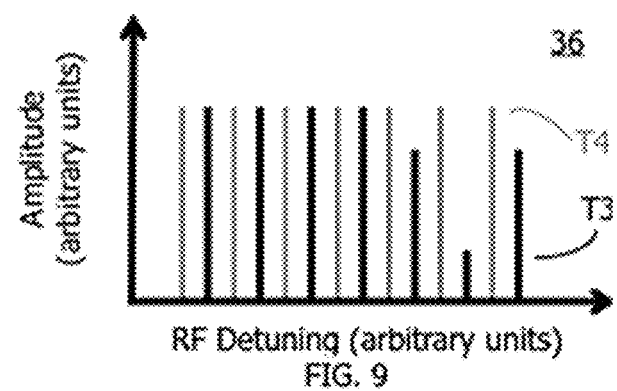
FIG. 9 shows a graph of amplitude versus RF detuning for an embodiment of an analyte spectrum.

Reference comb 30 shown in FIG. 7 is used to normalize sample comb 32 shown in FIG. 8. Additionally, reference comb 30 and sample comb 32 are combined by first combiner 64 to produce composite comb 34, which is combined with second comb 26 from local oscillator arm 66 by second combiner 68 to produce analyte spectrum 36. Analyte spectrum 36 is received by receiver 74 and processed to determine the radiofrequencies associated with the plurality of heterodyne frequencies in analyte spectrum 36. FIG. 9 shows a graph of amplitude versus RF detuning for an exemplary analyte spectrum 36. Here, analyte spectrum 36 includes a variation in amplitude of teeth T3 that corresponds, e.g., to absorption of radiation in probe comb 28 by sample 58. It should be appreciated that the analyte spectrum 36 is generated from a more complex spectrum that includes frequency teeth from a combination of first teeth T1 from both sample comb 32 and reference comb 30 heterodyned with second teeth T2 from second comb 26. The heterodyne results in a radiofrequency comb in FIG. 9, where first teeth from sample comb 26 are down-converted by second teeth T2 into the analyte teeth T3 and first teeth from reference comb 30 are down-converted by second teeth T2 into the radio frequency reference teeth T4. In an embodiment, numerical analysis of the more complex spectrum to produce analyte spectrum 32 is performed similarly to the process described in Long et al., "Multiheterodyne Spectroscopy with Optical Frequency Combs Generated from a Continuous-wave Laser," Optics Letters 39, 2688 (2014), the disclosure of which is incorporated by reference herein in its entirety. In an embodiment, second comb 26 is used to shift probe comb 28 or sample comb 32 into the RF domain where it can be digitized to provide high-speed multiplexing.

The comb source and heterodyne sensor described herein have advantages in comparison to conventional frequency scanning continuous-wave methods. For example, matching a laser cavity construction of two MLL FOFCs for performing conventional multi-heterodyne spectroscopy limits such an arrangement's broad dissemination and post-construction application. In an embodiment, beneficially, an entire absorption spectra of an analyte species is simultaneously recorded without dead time due to wavelength scanning. Furthermore, the continuous wave frequency source is, e.g., a diode laser and the like, and operation of the comb source or heterodyne sensor does not depend upon the continuous wave frequency source being a mode-locked femtosecond laser. Optical frequency combs (e.g., first comb 24 and second comb 26) include a plurality of teeth that, instead of being millions of teeth, include less than 10000 teeth, specifically less than 100 teeth, and more specifically less than 60 teeth in some embodiments. Accordingly, the optical power in a given comb tooth is greater than 1 microwatts ($\mu$W), which provides a high sensitivity limit for heterodyne sensor 50 and advantageously provides a selectively tailorable bandwidth of first comb 24 and second comb 26 (and therefore probe comb 28 and reference comb 30). Additionally, the heterodyne receiver 74 will detect phase coherent heterodyne signals in an absence of phase locking between multiple optical frequency combs. Furthermore, first comb 24 and second comb 26 can have a variable repetition rate and variable comb intensity. Frequency spacing among teeth in first comb 24 and second comb 26 as well as a relative amplitude of first teeth T1 and second teeth T2 can be precisely controlled and optimized at a high speed. According to an embodiment, comb source 2 or heterodyne sensor 50 is entirely fiber coupled and readily ruggedized.

The comb source 2 and heterodyne sensor 50 have many uses. According to an embodiment, comb source 2 includes electro-optic phase modulators such as dual Mach-Zehnder modulators to produce phase coherent optical frequency combs (24 and second comb 26) that have an arbitrary tooth spacing or arbitrary spectral bandwidth. Comb source 2 also can include an arbitrary waveform generator (AWG) as continuous wave frequency source 4 as well as a frequency multiplier or amplifiers to generate shaped waveforms (e.g., the first waveform or the second waveform) to drive the electro-optic phase modulators (or the I or Q independently of the Mach-Zehnder modulators) for control of the number of comb teeth (first comb teeth T1 or second comb teeth T2) and the intensity distribution across the combs (first comb 24 or second comb 26). Further, the comb source 2 having AWG is configured to generate chirped pulses that are phase coherent at the heterodyne receiver 74. First comb 24 and second comb 26 are produced from the continuous wave radiation from continuous wave frequency source (e.g., continuous wave laser source) and therefore can achieve up to 100% duty cycle. Unexpectedly, first comb 24 and second comb 26 have a selectively variable frequency tooth spacing (i.e., first frequency spacing F1 and second frequency spacing F2), and comb source 2 is configured to produce first comb 26 and second comb 24 that can be chirped while maintaining phase coherence at the heterodyne receiver 74. In contrast, conventional optical frequency combs produced from a phase coherent pulsed laser have less than 0.01% duty cycle and a fixed tooth spacing due to a round-trip rate through an optical resonator such that the conventional combs cannot be chirped with phase coherence.

First comb 24 and second comb 26 have different frequency spacing among first teeth T1 and second teeth T2 and can be combined (e.g., at second combiner 68) to produce analyte spectrum 36 that has a plurality of resolved down-converted (difference) frequencies for radiofrequency detection of sample comb 32 across a spectral region greater than hundreds of GHz.

In an embodiment, first comb 24 is frequency offset from second comb 26 prior to being combined at second combiner 68. In this manner, different frequencies associated with plus and minus sideband teeth of first comb 24 and second comb 26 are resolved unambiguously and doubles an amount of spectral coverage C. Reference comb 30 communicated in reference arm 62 bypasses sample 58 to be combined with the second comb 26 from local oscillator arm 66 to provide signal normalization. When tooth-to-tooth amplitude variations are sufficiently slow relative to variations caused by sample absorption, both first comb 24 and second comb 26 can pass through sample to preserve phase coherence at the heterodyne receiver 74. The arbitrary waveform generator of continuous wave frequency source 4 drives the electro-optic modulators (EOMs, e.g., first modulator 6 and second modulator 8 or I and Q of first Mach-Zehnder modulator 6 and second Mach-Zehnder modulator 8) and provides use and control of harmonics and phase shifts to control an intensity distribution of a comb output of the EOMs and to create shaped waveform pulses for comb generation in an frequency or amplitude modulated fashion. In this manner, comb spacing and bandwidth generated by the EOM(s) are controlled and selectively tailorable to augment a spectral resolving power or bandwidth coverage of comb source 2. Waveforms from comb source 2 also can be chirped to enhance spectral coverage and to enable precise speed or velocity measurements of a remote target.

According to an embodiment, heterodyne sensor 50 is configured to provide absorption spectroscopy or emission spectroscopy. Probe input 56 of probe arm 54 is connected, e.g., to a single pass cell, multi-pass cell, a remote sensing system and the like. In an embodiment, heterodyne sensor 50 is configured to perform cavity enhanced or cavity ring-down spectroscopy in a resonant optical cavity.

In an embodiment, continuous wave frequency source 4 is a single continuous wave laser to produce first comb 24 (provided to probe arm 54 and reference arm 62) and also to produce second comb 26 (provided to local oscillator arm 66). Since, in some embodiments, a same continuous wave frequency source 4 is used to produce first comb 24 and second comb 26, the plurality of first teeth T1 and plurality of second teeth T2 include narrow width, high amplitude teeth (T1 or T2) that are transform limited by a measurement time of analyte spectrum 36, i.e., the phase coherent heterodyne signal at receiver 74 produced from composite comb 34 and second comb 26.

Advantageously, heterodyne sensor 50 is configured to simultaneously measure absorption of a plurality of individual optical frequencies, e.g., from tens to thousands of optical frequencies. Further, heterodyne sensor 50 has high sensitivity and frequency precision for such measurements.

In an embodiment, first modulator 6 produces a plurality of sideband frequencies (i.e., teeth) on the continuous wave radiation (also referred to as an initial carrier frequency). First teeth T1 are spaced by first frequency spacing F1, i.e., a modulation frequency of the first waveform provided to first modulator 6 from waveform driver 10. By varying the amplitudes of the I and Q Mach-Zehnder drive signals as well as a DC bias applied to first modulator 6, relative amplitudes of first teeth T1 are controlled to produce first comb 24 having a selective frequency width and also having first teeth T1 with leveled amplitudes. As used herein, "leveled amplitudes" refers to the amplitudes for the first teeth being substantially similar or identical. It is contemplated that, for leveled amplitudes, a majority of first teeth T1 have substantially similar amplitudes. It also is contemplated that, for leveled amplitudes, some of the first teeth T1 can have different amplitudes from one another.

Sample 58 (e.g., a gas sample placed within a single pass cell, multi-pass cell, optical cavity, the optical path of a remote sensing system and the like) is subjected to probe comb 28. To determine simultaneously a local absorption at each comb tooth, second comb 26 will is communicated through local oscillator arm 66 to serve as a local oscillator. Second comb 26 has a modulation frequency that differs from sample comb 54 by, e.g., 10 kHz or the like. When sample comb 32 and second comb 26 are combined, e.g., on a high-speed photodiode, radiofrequency heterodyne beat frequencies are received by receiver 74 for each individual tooth T1 of probe comb 28. Additionally, acousto-optic modulator (e.g., first acousto-optic modulator 80 or second acousto-optic modulator 82 shifts the heterodyne beat frequencies into a radiofrequency range, e.g., 100 MHz.

In an embodiment, the heterodyne sensor 50 has a high acquisition rate, with a duty cycle near 100%, and provides ultra-sensitive measurements of sample 58, which can be, e.g., a short-lived species. Moreover, acquisition rate limits a drift in sampling conditions. According to an embodiment, the heterodyne sensor 50 is configured to perform spectroscopy, chemical dynamics studies, point source monitoring, remote sensing, and the like. In a particular embodiment, the heterodyne sensor 50 is configured to perform a cavity ring-down measurement. Here, probe comb 28 pumps sample 58 disposed in an optical cavity. Light is extinguished with an acousto-optic modulator or by EOM waveform control, causing the light leaking out of the cavity to decay. Sample comb 32 includes the decaying light and is combined with second comb 66 from local oscillator arm 66 on a high-speed photodiode. Analysis (e.g., a Fourier transform) of the combined combs provides a plurality of peaks that correspond to transmitted optical frequencies from sample 58. Widths W of the comb teeth are proportional the optical cavity decay rates (i.e., ring-down rates) and yield a local absorption and dispersion signals of sample 58.

The articles and processes herein are illustrated further by the following Examples, which are non-limiting.

EXAMPLES

Example 1. Production of Optical Frequency Combs from Continuous Wave Radiation

Figure 10:
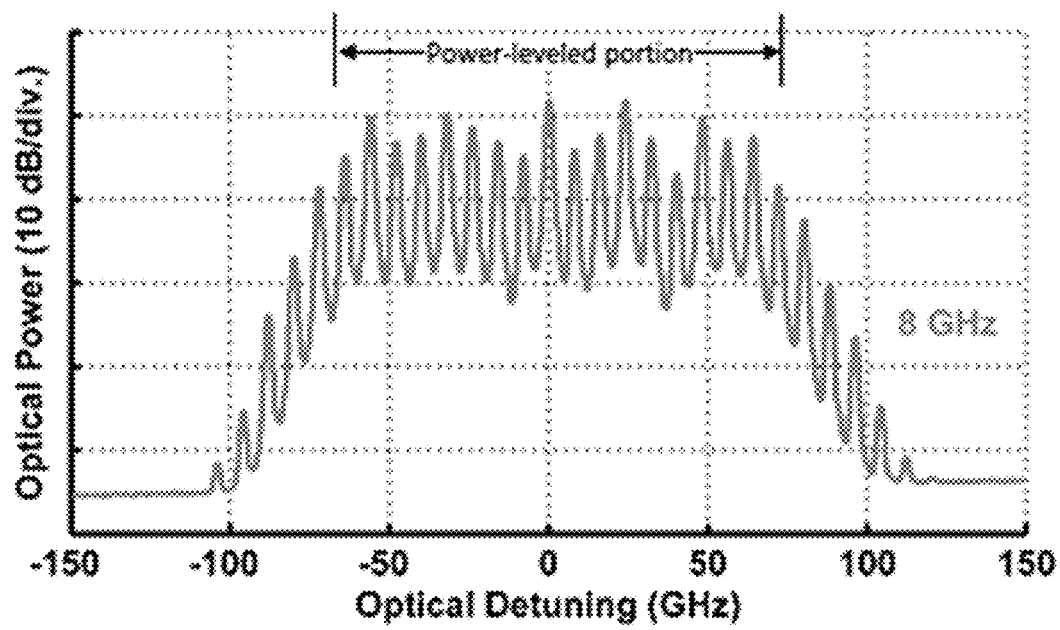
FIG. 10 shows a graph of optical power versus detuning for an embodiment of an optical frequency comb that has a frequency spacing of 8 GHz according to Example 1.
Figure 11:
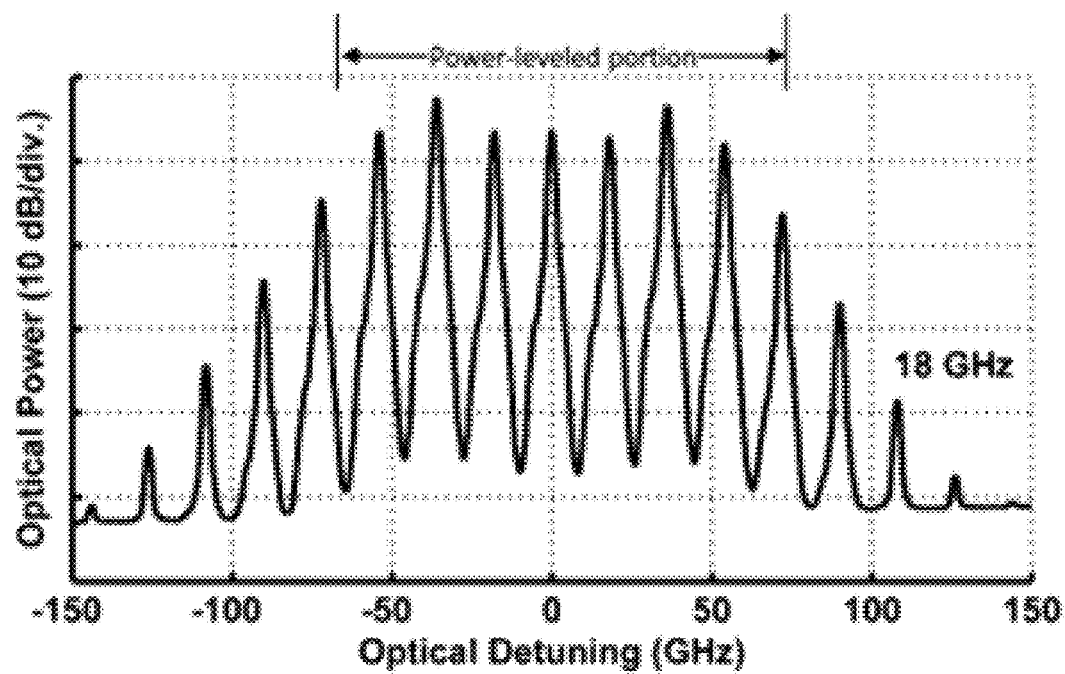
FIG. 11 shows a graph of optical power versus detuning for an embodiment of an optical frequency comb that has a frequency spacing of 18 GHz according to Example 1.

Optical frequency combs (OFCs) were produced using dual-drive Mach-Zehnder modulators (MZMs, 20 GHz bandwidth). The dual-drive MZMs levelled the optical power of the resultant OFCs by attenuation of one (I or Q) of the input waveforms input into the MZMs to drive and by control a phase condition with use of an external DC bias. These parameters were set prior to a given measurement with no active feedback. FIGS. 10 and 11 show a graph of optical power versus detuning for an optical frequency comb having an 8 GHz teeth frequency spacing (FIG. 10) and 18 GHz teeth frequency spacing (FIG. 11) acquired by an optical spectrum analyzer that had a resolution of 4 GHz. The asymmetric lineshape of the teeth was a result of a limitation of the spectrum analyzer: the widths of the comb teeth are limited by the length of the time domain record. Changing various microwave components produce optical frequency combs that had teeth frequency spacing from near DC to over a time scale provided by a tuning speeds of a waveform driver, e.g., a microwave source that had a 100 μs tuning speed. FIGS. 10 and 11 also show a power-leveled portion of the respective optical frequency combs. Here, the 8 GHz frequency spaced teeth of the optical frequency comb shown in FIG. 10 includes less than 20 teeth that were power-leveled and less than a total of 30 teeth. The 18 GHz frequency spaced teeth of the optical frequency comb shown in FIG. 11 includes less than 8 teeth that were power-leveled and less than a total of 20 teeth.

Example 2. Multiheterodyne Spectroscopy

Two OFCs (a probe comb and LO comb) were produced were produced from a single external-cavity diode laser using two dual drive MZMs. The probe comb and LO comb had comb frequency spacings that differed by $\delta f_{mod}$=24 kHz. A sample comb was produced by passing the probe comb through a sample of $CO_2$ gas. A fiber-coupled acousto-optic modulator (AOM) shifted the frequency of the probe comb by 99.9 MHz to move a heterodyne signal away from DC. Shifting the frequency of the probe comb reduced effects of 1/f noise and ensured each pair of optical frequency components (teeth) corresponded to a unique RF frequency.

Figure 12:
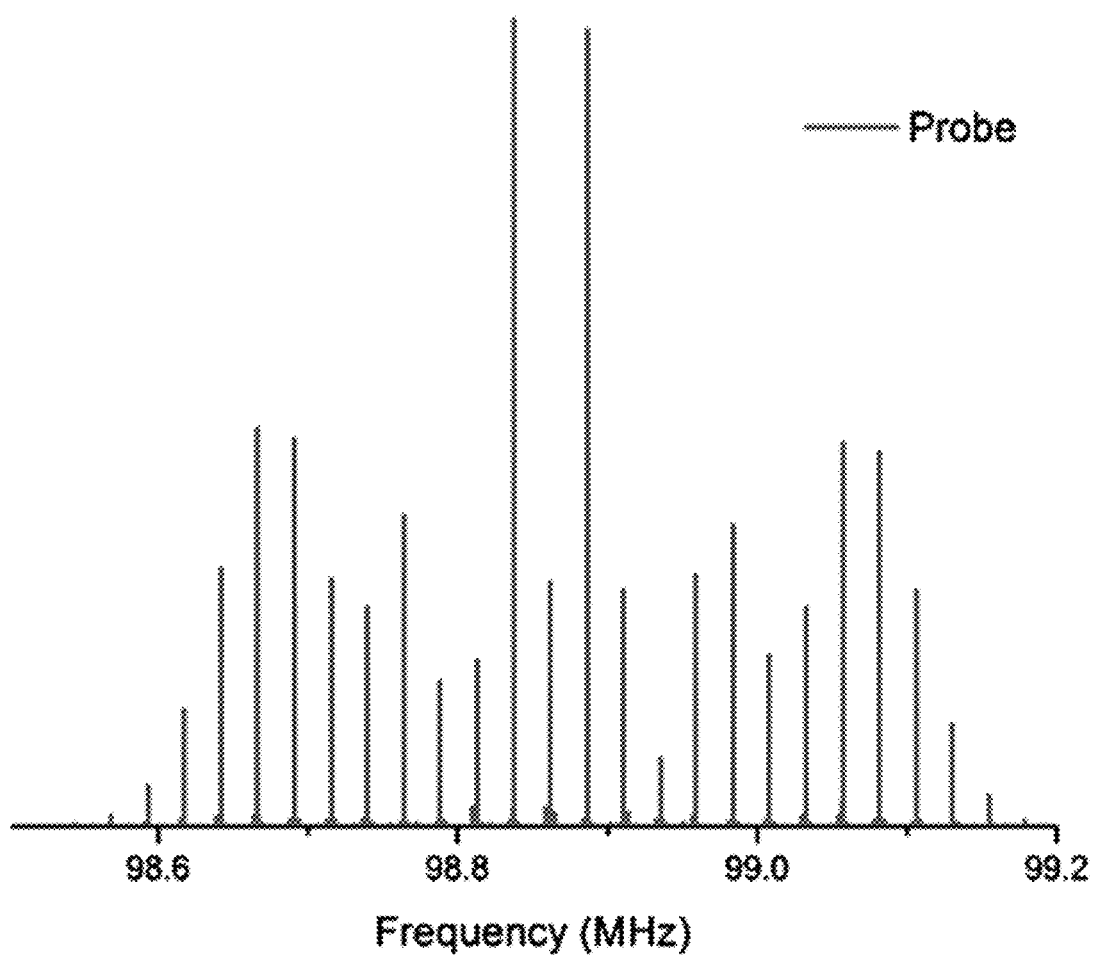
FIG. 12 shows a graph of intensity versus frequency for a sample comb obtained from passing a probe comb through a $CO_2$ sample according to Example 2.
Figure 13:
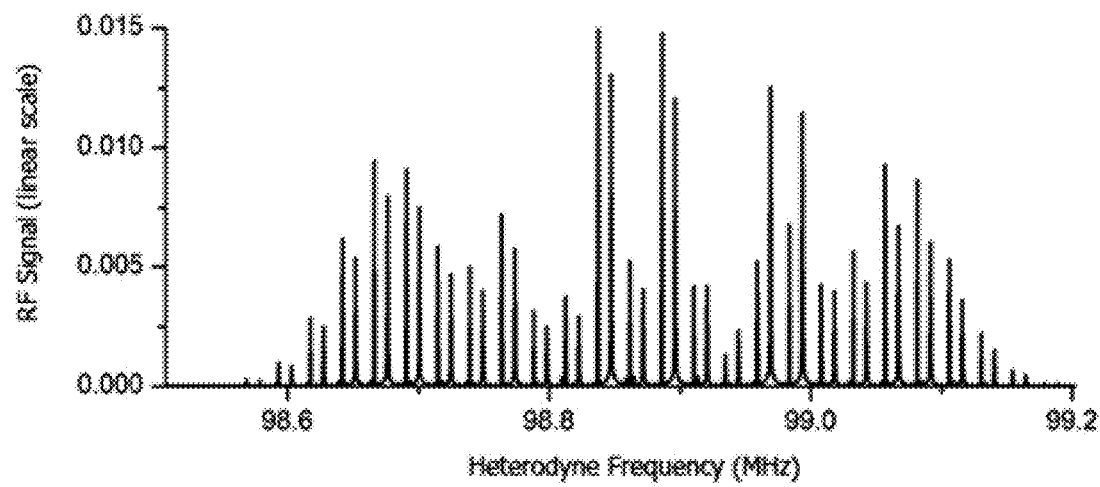
FIG. 13 shows a graph of RF signal versus heterodyne frequency according to Example 2

FIG. 12 shows a graph of intensity versus frequency for the probe comb after passing through the sample. To normalize a probe-LO heterodyne signal, a reference OFC was provided that did not interact with the gas sample. Driving the probe and reference comb AOMs at slightly different frequencies ($\delta f_{AOM}$=12 kHz) produced two interleaved heterodyne signals as shown in FIG. 13 for a frequency spectrum that corresponded to a magnitude of a Fourier-transformed time-domain signal. A ratio of an n-th pair of frequency components yielded a normalized transmission signal at a frequency of the probe comb, $f_{n,probe}$, which was a complex quantity containing phase and amplitude information. The magnitude of the transmission signal was proportional to a field amplitude of the probe comb after passing through the sample and equaled a square root of the transmission signal normally measured as a ratio of intensities. The phase of the heterodyne signal also was sensitive to a dispersive phase shift of the probe comb, which was caused by propagation of the probe comb through the sample.

Transmission measurements were made using two different absorption cells as a sample container that included a fiber-coupled multipass cell and a high-finesse optical cavity. The multipass cell had a total path length of 80 cm (five passes) and was filled with 13 kPa of $CO_2$. The spectrometer with the fiber-coupled multipass cell was entirely fiber-coupled and therefore ruggedized. Absorption spectra were recorded with a variety of comb spacings and yielded a single-element noise-equivalent absorption coefficient (NEA) of $2 \times 10^{-5}$ cm$^{-1}$ Hz$^{-1/2}$. To improve detection sensitivity, additional measurements were made using an optical cavity of length 74 cm having an empty-cavity finesse of 20,000. The single element NEA was thus improved to $3 \times 10^{-10}$ cm$^{-1}$ Hz$^{-1/2}$.

To ensure constant and efficient coupling of the OFC into the optical cavity, the carrier frequency of the probe comb was Pound-Drever-Hall locked to the optical cavity with a locking bandwidth of 1 MHz, which provided a linewidth of 130 Hz relative to the optical cavity. The frequency spacing of the teeth of the probe comb was set to a multiple of the cavity's free spectral range (203.076 MHz) to provide simultaneous cavity transmission of all probe comb frequency components.

Data for absorption for $CO_2$ (transition (30013)←(00001) R16e) at 14 Pa was acquired. An amplitude of the observed multiheterodyne signal resulting from the interference of the OFCs was recorded. The multiheterodyne signal was an average of 10,000 individual measurements, which were recorded on a 14-bit spectrum analyzer with a resolution bandwidth of 1 kHz in a total acquisition time of 30 seconds. The combs were directed to be incident on a photodiode. The total optical power on the photodiode was 11.6 µW. Note that due to the common-mode nature of this multiheterodyne signal, widths of individual radiofrequency (teeth) features were resolution-limited at a bandwidth of 1 Hz. A ratio of each probe comb tooth (i.e., frequency component) and corresponding reference frequency component provided a local, complex, normalized transmission signal. FIG. 13 shows a graph of RF signal versus heterodyne frequency of the data.

Figure 14:
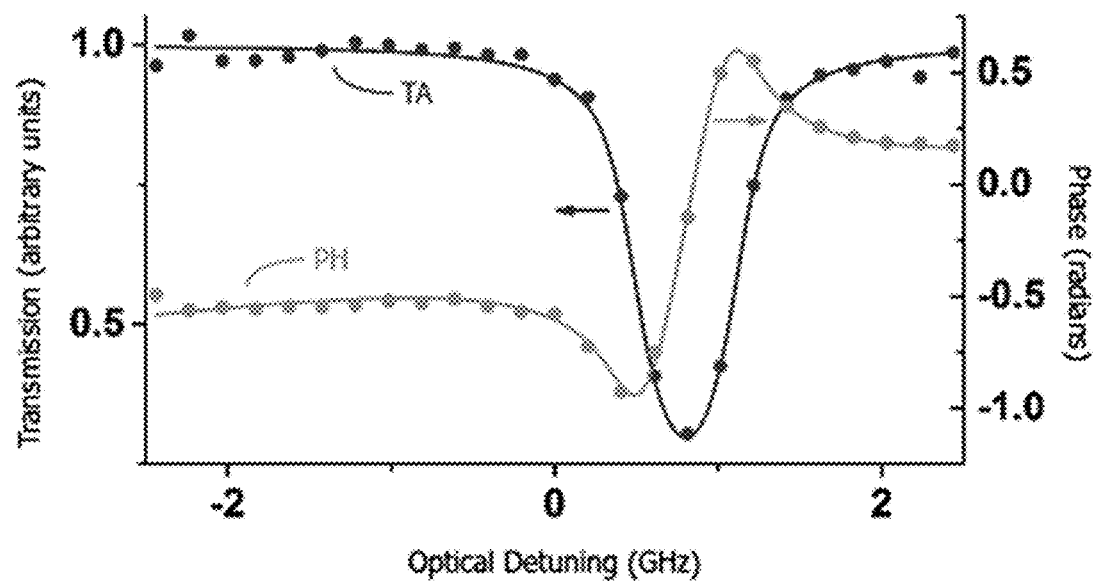
FIG. 14 shows a graph of transmission and phase versus optical detuning according to example 2 and FIG. 15 shows a graph of transmission versus detuning for a sample of methane according to Example 3

FIG. 14 shows a graph of transmission versus optical detuning for baseline-corrected transmission amplitude (TA) and phase (PH) spectra. The two solid lines are curves that resulted from a simultaneous fit to the measured amplitude and phase spectra that treated the gas pressure, carrier detuning from line center, baseline amplitude, and phase as adjustable parameters.

Example 3. Triple Comb Multiheterodyne Spectroscopy

Optical frequency combs were produced according to the scheme shown in FIGS. 3, 4, 5 using two electro-optic phase modulators. The waveform frequencies M of first comb 24 and second comb 26 were 666.66667 MHz and 666.61667 MHz, respectively. The period of first comb is 54 nsec to generate fine teeth with spacing 18.518 MHz and the period of the second comb (LO comb) is the same as the sampling period of 2.4192 ms. The pulse shapes were initially optimized (in an iterative way using genetic algorithms) by variation of the amplitudes, phases and widths of the fundamental and two harmonics over the sampling period. The resulting heterodyne waveform at receiver 74 is Fourier transformed to give independent sets of radiofrequency combs for each of the probe and reference arms. The AOM shifts used in probe arm 54 and reference arm 62 were 251.010 MHz and 251.000 MHz, respectively, separating the probe and corresponding reference teeth in the heterodyne signal by 10 kHz. Similar to that described in Example 2, the heterodyne signal from the sidebands of the first comb and second comb also define two (primary) sets of course teeth that have a frequency spacing of 50 kHz and centered at 251.010 MHz and 251.00 MHz for the probe and reference combs, respectively. In this embodiment, two secondary sets of course teeth result with the same 50 kHz spacing and are centered at 415.606 MHz and 415.616 MHz for the probe and reference combs, respectively. The radiofrequency multiheterodyne spectrum obtained from the secondary sets is reversed and offset by −2.07 MHz relative to that from the primary sets. Each of the four combs contain nearly 700 teeth covering a 13.3 GHz region. For each set, the probe and reference combs are sorted, integrated and then normalized to the corresponding reference signals.

Figure 15:
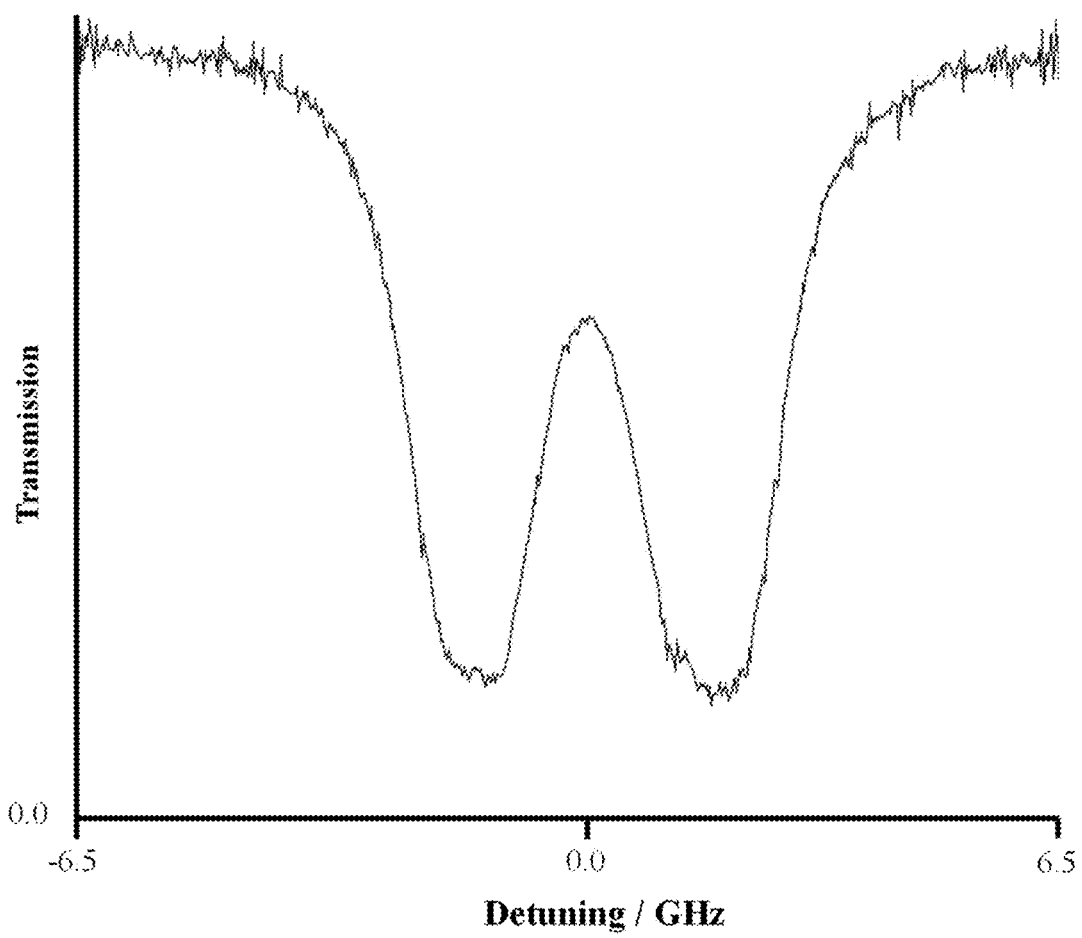

The amplitude transmission versus detuning of a multiheterodyne analyte spectrum of $CH_4$ at 6077 cm$^{-1}$ is shown in FIG. 15. The spectrum was obtained using 25 cm long sample cell filled with 16 kPa of methane at room temperature and was acquired in 40 ms at a step resolution of 18.5 MHz. The integrated intensity and doublet structure are in good agreement with predictions from the HITRAN database. The fine tooth spacing and the easy of which the spacing can be varied across a wide range (<1 MHz to >20 GHz) increases the utility of this method for high resolution applications and is nearly impossible to achieve using other methods.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A comb source comprising:
    a continuous wave frequency source to provide a continuous wave radiation;
    a first modulator in optical communication with the continuous wave frequency source to receive the continuous wave radiation;
    a second modulator in optical communication with continuous wave frequency source to receive the continuous wave radiation; and
    a waveform driver in electrical communication with the first modulator and the second modulator to provide a first waveform to the first modulator and a second waveform to the second modulator, the first waveform and the second waveform independently comprising:
        a variable amplitude; and
        a variable frequency or plurality of harmonic frequencies.

2. The comb source of claim 1, wherein the first modulator is configured to produce a first comb in response to receipt of the first waveform and the continuous wave radiation.

3. The comb source of claim 2, wherein the second modulator is configured to produce a second comb in response to receipt of the second waveform and the continuous wave radiation.

4. The comb source of claim 3, wherein the first comb comprises a plurality of first teeth;
    the second comb comprises a plurality of second teeth;
    the first teeth are spaced apart by a first frequency spacing; and
    the second teeth are spaced apart by a second frequency spacing.

5. The comb source of claim 4, wherein the first frequency spacing and the second frequency spacing independently are selectively variable, respectively based on the first waveform and the second waveform from the waveform driver.

6. The comb source of claim 5, wherein the first frequency spacing and the second frequency spacing are independently selectively tunable from 1 kHz to 50 GHz.

7. The comb source of claim 6, wherein the first frequency spacing is different than the second frequency spacing.

8. The comb source of claim 5, wherein the first comb and the second comb independently are a power-leveled optical frequency comb.

9. The comb source of claim 5, wherein the first teeth comprise a width that is less than 1 kilohertz (kHz), and the second teeth comprise a width that is less than 1 kHz.

10. The comb source of claim 1, wherein the waveform driver is an arbitrary waveform generator or a frequency synthesizer.

11. The comb source of claim 10, wherein the waveform driver is the frequency synthesizer, and the variable frequency is a microwave frequency.

12. The comb source of claim 1, wherein the first modulator and the second modulator independently are an electro-optic modulator comprising a phase modulator, Pockels cell, a Mach-Zehnder modulator, or a combination comprising at least one of the foregoing modulators.

13. The comb source of claim 1, wherein the continuous wave frequency source is a continuous wave laser comprising a wavelength from 200 nm to 100000 nm.

14. A heterodyne sensor comprising:
    the comb source of claim 5;
    a splitter to receive the first comb and configured to split the first comb into a probe comb and a reference comb;
    a probe arm to receive the probe comb and comprising:
        a probe input configured to communicate the probe comb to a sample; and
        a probe output to receive a sample comb;
    a reference arm to receive the reference comb;
    a first combiner to receive the reference comb and the sample comb and configured to produce a composite comb from the reference comb and the sample comb;
    a local oscillator arm to receive the second comb; and
    a second combiner to receive the second comb from the local oscillator and the composite comb and configured to produce an analyte spectrum from the second comb and the composite comb.

15. The heterodyne sensor of claim 14, wherein the probe output comprises a first acousto-optic modulator to receive the sample comb, and the reference arm comprises a second acousto-optic modulator to receive the reference comb.

16. The heterodyne sensor of claim 14, wherein the analyte spectrum comprises a plurality of heterodyned frequencies.

17. The heterodyne sensor of claim 16, wherein the plurality of heterodyned frequencies comprises a radiofrequency.

* * * * *